United States Patent [19]

Lorenz et al.

[11] 3,970,665

[45] *July 20, 1976

[54] BENZISOXAZOLO (THIONO)PHOSPHORIC(PHOSPHONIC) ACID ESTERS

[75] Inventors: Walter Lorenz, Wuppertal, Cronenberg; Horst Böshagen, Haan, Rhineland; Ingeborg Hammann; Wolfgang Behrenz, both of Cologne, all of Germany

[73] Assignee: Bayer Aktiengesellschaft, Leverkusen, Germany

[ * ] Notice: The portion of the term of this patent subsequent to June 25, 1991, has been disclaimed.

[22] Filed: Dec. 3, 1973

[21] Appl. No.: 421,319

Related U.S. Application Data

[63] Continuation of Ser. No. 169,498, Aug. 5, 1971, abandoned.

[30] Foreign Application Priority Data

Aug. 14, 1970 Germany.............................. 2040410

[52] U.S. Cl. ........................... 260/307 DA; 424/200
[51] Int. Cl.² ......................................... C07D 261/20
[58] Field of Search ................................ 260/307 D

[56] References Cited
UNITED STATES PATENTS

3,828,063  8/1974  Lorenz et al.................... 260/307 D

FOREIGN PATENTS OR APPLICATIONS

2,040,410  2/1972  Germany 965,997  8/1964  United Kingdom

*Primary Examiner*—Raymond V. Rush
*Attorney, Agent, or Firm*—Burgess, Dinklage & Sprung

[57] ABSTRACT

Benzisoxazolo(thiono)phosphoric(phosphonic) acid esters of the general formula

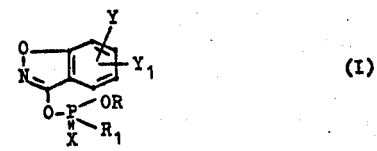

in which
X is oxygen or sulfur,
R is an alkyl radical with 1-6 carbon atoms,
$R_1$ is an alkyl or alkoxy radical with 1-6 carbon atoms,
Y is an alkyl, alkoxy, alkylmercapto or nitro radical, and
$Y_1$ is a hydrogen, alkyl, alkoxy, alkylmercapto or nitro radical or, when Y is an alkyl radical, a chlorine atom, which possess insecticidal, acaricidal, nematocidal, fungicidal and tickicidal properties.

A representative compound is O,O-dimethyl-0-[7-methylbenzisoxazol(3)yl]-thionophosphoric acid ester.

5 Claims, No Drawings

BENZISOXAZOLO (THIONO)PHOSPHORIC(PHOSPHONIC)ACID ESTERS

This is a continuation of application Ser. No. 169,498, filed Aug. 5, 1971, now abandoned.

The present invention relates to and has for its objects the provision of particular new benzisoxazolo(thiono, phosphoric(phosphonic) acid esters, i.e. O-alkyl-(thiono) phosphoric(phosphonic) acid esters of 3-hydroxybenzisoxazole carrying on the benzene ring one or two alkyl, alkoxy, alkylmercapto or nitro radicals or one chloro plus one alkyl radical, which possess insecticidal, acaricidal, nematocidal, tickicidal and fungicidal properties, active compositions in the form of mixtures of such compounds with solid and liquid dispersible carrier vehicles, and methods for producing such compounds and for using such compounds in a new way especially for combating pests, e.g. insects, acarids, nematodes, ticks and fungi, especially insects and acarids, with other and further objects becoming apparent from a study of the within specification and accompanying examples.

It is already known from German Published Specification 1,253,713 that certain chloro-substituted benzisoxazolo(thiono)phosphoric acid esters, such as O,O-dimethyl- or O,O-diethyl-0-(5-chlorobenzisoxazol(-3)yl)-thionophosphoric acid ester (Compounds A and B, respectively) or O,O-diethyl-0-(5-chlorobenzisoxazol-(3)yl)-phosphoric acid ester (Compound C), exhibit insecticidal properties.

The present invention provides, as new compounds, the benzisoxazolo(thiono)phosphoric(phosphonic) acid esters of the general formula

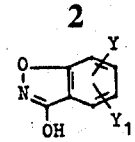
(I)

in which

X is oxygen or sulfur,

R is an alkyl radical with 1-6 carbon atoms, $R_1$ is an alkyl or alkoxy radical with 1-6 carbon atoms, Y is an alkyl, alkoxy, alkylmercapto or nitro radical, and $Y_1$ is a hydrogen, alkyl, alkoxy, alkylmercapto or nitro radical or, when Y is an alkyl radical, a chlorine atom.

These new compounds have been found to possess strong insecticidal and acaricidal, as well as nematocidal, tickicidal and fungicidal, properties.

The present invention also provides a process for the preparation of a compound of the formula (I), in which a 3-hydroxy-benzyisoxazole of the general formula

(II)

is reacted, either in the presence of an acid-acceptor or in the form of an alkali metal, alkaline earth metal or ammonium salt, with a (thiono)phosphoric(phosphonic) acid ester halide of the general formula $$\underset{R_1}{\overset{RO}{>}}\overset{X}{\underset{\|}{P}}-Hal \qquad (III)$$

in which formulae

Y, $Y_1$, R, $R_1$ and X have the meanings stated above for formula (I), and

Hal is a halogen atom, preferably a chlorine atom.

Surprisingly, the benzisoxazolo(thiono)phosphoric (phosphonic) acid esters according to the invention show a substantially better insecticidal, soil-insecticidal and acaricidal activity, and in some cases nematocidal and fungicidal activity, than the known chloro-substituted benzisoxazolo(thiono)phosphoric acid esters of analogous constitution and the same direction of activity. The compounds according to the invention therefore represent a genuine enrichment of the art.

If O,O-diethylthionophosphoric acid ester chloride and 3-hydroxy-6-nitro-benzisoxazole are used as starting materials, the reaction course can be represented by the following equation:

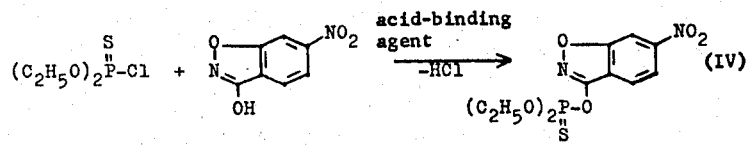

(IIIa)   (IIa)   (I)

Preferably, R is a straight-chain or branched alkyl radical with 1-4 carbon atoms, namely methyl, ethyl, n- or iso-propyl or n-, iso-, sec.- or tert.-butyl, andd $R_1$ is a straight-chain or branched alkyl radical with 1-4 carbon atoms as enumerated above or an alkoxy radical with 1-4 carbon atoms, namely methoxy, ethoxy, n-or isopropoxy or n-, iso-, sec.- or tert.-butoxy. Preferably, Y is nitro or alkyl, alkoxy or alkylmercapto with, in each case, 1-4 carbon atoms and $Y_1$ is chloro with Y being alkyl or nitro. When Y is alkyl, alkoxy or alkylmercapto the alkyl groups preferably have 1-4 carbon atoms.

As examples of the benzisoxazole derivatives which can be used as starting materials, there may be mentioned: 5-nitro-, 6-nitro-, 5,7-dinitro-, 6-methyl-, 7-methyl-, 5-tert.-butyl-, 5-methoxy-, 6-methoxy-, 6-propoxy-, 5-isopropoxy-, 5-isopropyl-, 6-isopropyl-, 5-ethoxy-, 5-methyl- mercapto-, 6-methylmercapto, 5-ethylmercapto-, 6-ethylmercapto, 5-isopropylmercapto-, 6-isopropylmercapto-, 5-methylmercapto- 6-methyl, 5-ethylmercapto-6-methyl-, 5-methylmercapto-6-propyl-, 5-chloro-7-ethyl-, 5-chloro-7-isopropyl-, 5-chloro-7-methyl- and 5-chloro-7-butyl-3-hydroxy-benzisoxazoles; and, As examples of (thiono)phosphoric(phosphonic) acid ester halides which can be used as starting materials there may be mentioned:

0,0-dimethyl-, 0,0-diethyl-, 0,0-dipropyl-, 0,0-di-isopropyl-, 0-methyl-0-ethyl-, 0-methyl-0-isopropyl-, 0-ethyl-0-isopropyl-, 0-methyl-0-butyl-, 0,0-dibutyl-, 0,0-di-isobutyl-, 0-tert.- butyl-0-methylphosphoric acid ester halides and the corresponding thiono analogoues and 0-methyl-methane-, 0-ethyl-propane-, 0-isopropyl-ethane-, 0-butyl-methane-, 0-methyl-isopropane-, 0-methyl-ethane-, 0-ethyl-ethane-, 0-propyl-methane-, 0butylethane-phosphonic acid ester halides and the corresponding thiono compounds.

The (thiono)phosphoric(phosphonic) acid esters used as starting materials are known and can be prepared according to customary processes, as can the 3-hydroxy-benzisoxazoles (see Chem. Ber. 100, 954 – 960 [1967]).

The preparative process is carried out preferably with the use of suitable solvents or diluents. As such, practically all inert organic solvents are suitable, especially aliphatic and aromatic optionally chlorinated hydrocarbons, such as benzene, toluene, xylenes, benzine, methylene chloride, chloroform, carbon tetrachloride, and chlorobenzene; ethers, such as diethyl ether, dibutyl ether, and dioxane; ketones, for example acetone, methylethyl, methylisopropyl and methylisobutyl ketones; and nitriles, such as acetonitrile and propionitrile.

As acid acceptors, all customary acid-binding agents can be used. Particularly good results have been obtained with alkali metal carbonates and alcoholates, such as sodium and potassium carbonates, methylates or ethylates, as well as with aliphatic, aromatic or heterocyclic amines, for example triethylamine, dimethylamine, dimethylaniline, dimethylbenzylamine and pyridine.

The reaction temperature can be varied within a fairly wide range. In general, the reaction is carried out at about 0° to 120°C, preferably at about 40° to 70°C. The reaction is, in general, carried out at normal pressure.

For the carrying out of the process, the starting materials are in most cases used in equimolar amounts. An excess of one or the other of the reaction components brings no substantial advantages. The reaction is preferably carried out in the presence of one of the abovementioned solvents, as well as in the presence of an acid acceptor (unless a salt of the compound of the formula (II) is used), within the temperature range stated; after several hours' stirring — possibly with heating — the reaction mixture may be worked up in any usual manner. The substances according to the invention are obtained in most cases in the form of colorless or colored, viscous, water-insoluble oils which cannot be distilled without decomposition but can, by so-called "slight distillation", that is by longer heating to moderately elevated temperatures under reduced pressure, be freed from the last volatile components and in this way be purified. For their characterization, the refractive index is especially suitable.

As already mentioned, the new benzisoxazolo(thiono) phosphoric(phosphonic) acid esters are distinguished by an outstanding insecticidal and acaricidal effectiveness against crop pests, pests harmful to health and pests of stored products. They possess a good activity against both sucking and biting insects and mites (Acarina). At the same time they exhibit a low phytotoxicity and, in some cases, also nematocidal, tickicidal and fungicidal properties.

For these reasons, the compounds according to the invention may be used with success as pesticides in crop protection and the protection of stored products, as well as in the hygiene and veterinary fields.

To the sucking insects contemplated herein there belong, in the main, aphids (Aphidae) such as the geen peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*; and the like.

In the case of the biting insects contemplated herein, above all there should be mentioned butterfly caterpillars (Lepidoptera) such as the diamond-back moth (Plutella maculipennis), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*); and the like.

Also to be classed with the biting insects contemplated herein are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle ((*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Acheta domesticus*); termites such as the eastern subterranean termite (*Reticulitermes flavipes*) and Hymenoptera such as ants, for example the garden ant (*Lasius niger*); and the like.

The Diptera contemplated herein comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*); and the like.

With the mites (Acarina) there are classed, in particular, the spider mites (Tetranychidae) such as the two-spotted spider mite (*Tetranychus telarius = Tetranychus althaeae* or *Tetranychus urticae*) and the European red mite (*Paratetranychus pilosus = Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*) finally, ticks, such as the relapsing fever tick (*Ornithodorus moubata*); and the like.

When applied against pests harmful to health and pests of stored products, particularly flies and mosquitoes, the compounds are also distinguished by an outstanding residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, etc.), halogenated, especially chlorinated, aromatic hydrocarbons (e.g. chlorobenzenes, etc.), paraffins (e.g. petroleum fractions), chlorinated aliphatic hydrocarbons (e.g. methylene chloride, etc.), alcohols (e.g. methanol, ethanol, propanol, butanol, etc.), amines (e.g. ethanolamine, etc.), ethers, ether-alcohols (e.g. glycol monomethyl ether, etc.), amides (e.g. dimethyl formamide, etc.), sulfoxides (e.g. dimethyl sulfoxide, etc.), ketones (e.g. acetone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other acaricides, insecticides, nematocides, fungicides and tickicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids, nematodes, ticks and fungi, and more particularly methods of combating at least one of insects and acarids, which comprises applying to at least one of correspondingly (a) such insects, (b) such acarids, (c) such nematodes, (d) such fungi, (e)

such ticks, and (f) the corresponding habitat thereof, i.e. the locus to be protected, a correspondingly combative or toxic amount, i.e. an insecticidally, acaricidally, nematocidally, fungicidally or tickicidally effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phaedon larvae test

Solvent: 3 parts by weight acetone
Emulsifier: 1 part by weight alkylaryl polyglycol ether To produce a suitable preparation of active compound, 1 part by weight of the active compound is mixed with the stated amount of solvent containing the stated amount of emulsifier, and the concentrate is diluted with water to the desired concentration.

Cabbage leaves (*Brassica oleracea*) are sprayed with the preparation of the active compound until dripping wet and then infested with mustard beetle larvae (*Phaedon cochleariae*).

After the specified periods of time, the degree of destruction is determined as a percentage: 100% means that all the beetle larvae are killed. 0% means that none of the beetle larvae are killed.

The active compounds, the concentration of the active compound, the times of evaluation and the results can be seen from the following Table 1:

Table 1

| Active compound (constitution) | Concentration of active compound in % | Degree of destruction in % after 3 days |
|---|---|---|
| (A) 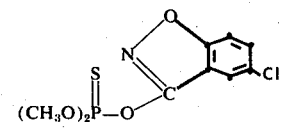 (known) | 0.1<br>0.01<br>0.001 | 100<br>100<br>0 |
| (B) 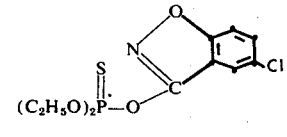 (known) | 0.1<br>0.01<br>0.001 | 100<br>100<br>0 |
| (C) 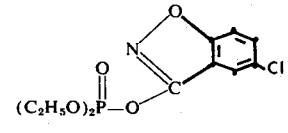 (known) | 0.1<br>0.01<br>0.001 | 100<br>90<br>0 |
| (2) 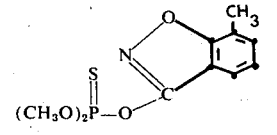 | 0.1<br>0.01<br>0.001 | 100<br>100<br>80 |
| (3) 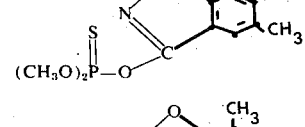 | 0.1<br>0.01<br>0.001 | 100<br>100<br>70 |
| (4) 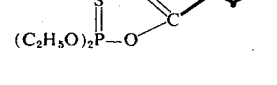 | 0.1<br>0.01<br>0.001 | 100<br>100<br>100 |
| (5) 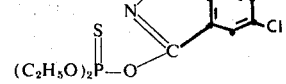 | 0.1<br>0.01<br>0.001 | 100<br>100<br>100 |

Table 1-continued

| Active compound (constitution) | (Phaedon larvae test) Concentration of active compound in % | Degree of destruction in % after 3 days |
|---|---|---|
| (6) [structure: (C₂H₅O)₂P(S)—O—C(=N)—O— benzene ring with SC₂H₅] | 0.1<br>0.01<br>0.001 | 100<br>100<br>100 |
| (1) [structure: (C₂H₅O)₂P(S)—O—C(=N)—O— benzene ring with NO₂] | 0.1<br>0.01<br>0.001 | 100<br>100<br>100 |

EXAMPLE 2

Plutella test

Solvent: 3 parts by weight acetone
Emulsifier: 1 part by weight alkylaryl polyglycol ether To produce a suitable preparation of active compound, 1 part by weight of the active compound is mixed with the stated amount of solvent containing the stated amount of emulsifier and the concentrate is diluted with water to the desired concentration.

Cabbage leaves (*Brassica oleracea*) are sprayed with the preparation of the active compound until dew moist and are then infested with caterpillars of the diamond-back moth (*Plutella maculipennis*).

After the specified periods of time, the degree of destruction is determined as a percentage: 100% means that all the caterpillars are killed whereas 0% means that none of the caterpillars are killed.

The active compounds, the concentrations of the active compounds, the evaluation times and the results can be seen from Table 2:

EXAMPLE 3

Myzus test (contact action)

Solvent: 3 parts by weight acetone
Emulsifier: 1 part by weight alkylaryl polyglycol ether To produce a suitable preparatin of active compound, 1 part by weight of the active compound is mixed with the stated amount of solvent containing the stated amount of emulsifier and the concentrate is diluted with water to the desired concentration.

Cabbage plants (*Brassica oleracea*) which have been heavily infested with peach aphids (*Myzus persicae*) are sprayed with the preparation of the active compound until dripping wet.

After the specified periods of time, the degree of destruction is determined as a percentage: 100% means that all the aphids are killed whereas 0% means that none of the aphids are killed.

The active compounds, the concentrations of the active compounds, the evaluation times and the results can be seen from the following Table 3:

Table 2

| Active compound (constitution) | (Plutella test) Concentration of active compound in % | Degree of destruction in % after 3 days |
|---|---|---|
| (C) (known) [structure: (C₂H₅O)₂P(=O)—O—C(=N)—O— benzene ring with Cl] | 0.1<br>0.01<br>0.001<br>0.0001 | 100<br>100<br>50<br>0 |
| (7) [structure: (C₂H₅O)₂P(S)—O—C(=N)—O— benzene ring with NO₂] | 0.1<br>0.01<br>0.001 | 100<br>100<br>100 |
| (8) [structure: (C₂H₅O)₂P(S)—O—C(=N)—O— benzene ring with C(CH₃)₃] | 0.1<br>0.01<br>0.001 | 100<br>100<br>90 |

Table 3

| | (Myzus test) Active compound (constitution) | Concentraton of active compound in % | Degree of destruction in % after 1 day |
|---|---|---|---|
| (A) | 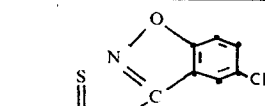 (known) | 0.1<br>0.01<br>0.001<br>0.0001 | 100<br>100<br>90<br>0 |
| (C) | 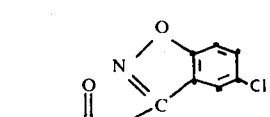 (known) | 0.1<br>0.01<br>0.001<br>0.0001 | 100<br>100<br>80<br>0 |
| (2) | 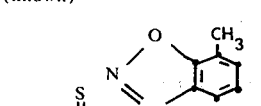 | 0.1<br>0.01<br>0.001<br>0.0001 | 100<br>100<br>100<br>70 |
| (3) | 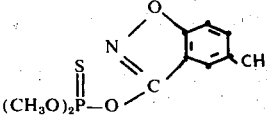 | 0.1<br>0.01<br>0.001<br>0.0001 | 100<br>100<br>98<br>40 |
| (4) | 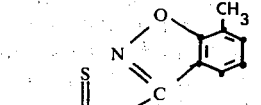 | 0.1<br>0.01<br>0.001<br>0.0001 | 100<br>100<br>100<br>95 |
| (9) | 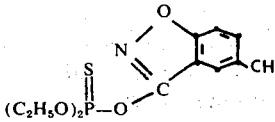 | 0.1<br>0.01<br>0.001<br>0.0001 | 100<br>100<br>100<br>80 |
| (5) | 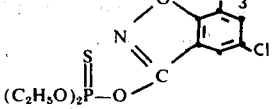 | 0.1<br>0.01<br>0.001<br>0.0001 | 100<br>100<br>100<br>95 |
| (1) | 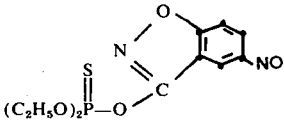 | 0.1<br>0.01<br>0.001<br>0.0001 | 100<br>100<br>98<br>85 |
| (7) | 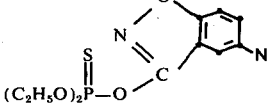 | 0.1<br>0.01<br>0.001<br>0.0001 | 100<br>100<br>100<br>70 |
| (10) | 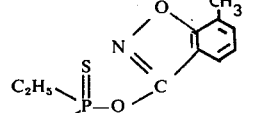 | 0.1<br>0.01<br>0.001<br>0.0001 | 100<br>100<br>100<br>98 |
| (11) | 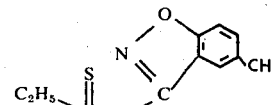 | 0.1<br>0.01<br>0.001<br>0.0001<br>0.00001 | 100<br>100<br>100<br>99<br>45 |

EXAMPLE 4

Tetranychus test

The active compounds, the concentrations of the active compounds, the evaluation times and the results can be seen from Table 4:

Table 4

(Tetranychus test)

| Active compound (constitution) | Concentration of active compound in % | Degree of destruction in % after 2 days |
|---|---|---|
| (A) [structure: (CH$_3$O)$_2$P(=S)—O—C(=N—O—)—C$_6$H$_3$—Cl] (known) | 0.1 | 0 |
| (2) [structure: (CH$_3$O)$_2$P(=S)—O—C(=N—O—)—C$_6$H$_3$—CH$_3$] | 0.1 | 60 |
| (4) [structure: (C$_2$H$_5$O)$_2$P(=S)—O—C(=N—O—)—C$_6$H$_3$—CH$_3$] | 0.1 | 60 |
| (9) [structure: (C$_2$H$_5$O)$_2$P(=S)—O—C(=N—O—)—C$_6$H$_3$—CH$_3$] | 0.1 | 60 |
| (6) [structure: (C$_2$H$_5$O)$_2$P(=S)—O—C(=N—O—)—C$_6$H$_3$—SC$_2$H$_5$] | 0.1 | 60 |
| (7) [structure: (C$_2$H$_5$O)$_2$P(=S)—O—C(=N—O—)—C$_6$H$_3$—NO$_2$] | 0.1 | 98 |

Solvent: 3 parts by weight acetone
Emulsifier: 1 part by weight alkylaryl polyglycol ether To produce a suitable preparation of active compound, 1 part by weight of the active compound is mixed with the stated amount of solvent containing the stated amount of emulsifier and the concentrate so obtained is diluted with water to the desired concentration.

Bean plants (*Phaseolus vulgaris*), which have a height of approximately 10–30 cm., are sprayed with the preparation of the active compound until dripping wet. These bean plants are heavily infested with spider mites (*Tetranychus urticae*) in all stages of development.

After the specified periods of time, the effectiveness of the preparation of active compound is determined by counting the dead mites. The degree of destruction thus obtained is expressed as a percentage: 100% means that all the spider mites are killed whereas 0% means that none of the spider mites are killed.

EXAMPLE 5

Phorodon humuli test (contact action)

Solvent: 3 parts by weight acetone
Emulsifier: 1 part by weight alkylarylpolyglycol ether To produce a suitable preparation of active compound, 1 part by weight of the active compound is mixed with the stated amount of solvent containing the stated amount of emulsifier, and the concentrate is diluted with water to the desired concentration.

Hop plants (*Humulus lupulus*) which have been heavily infested with the hop aphid (*Phorodon humuli*) are sprayed with the preparation of the active compound until dripping wet.

After the specified periods of time, the degree of destruction is determined as a percentage: 100% means that all the aphids were killed; 0% means that none of the aphids were killed.

The active compounds, the concentrations of the active compounds, the evaluation times and the results can be seen from the following Table 5:

Table 5
(Phorodon humuli test)

| Active compound (constitution) | Concentration of active compound in % | Degree of destruction in % after 1 day |
|---|---|---|
| (C) Cl-[aryl]-O-N=C-O-P(OC$_2$H$_5$)$_2$ (carbonyl) (known) | 0.02 / 0.004 / 0.0008 / 0.00016 / 0.000032 | 100 / 95 / 95 / 90 / 65 |
| (9) CH$_3$-[aryl]-O-N=C-S-P(OC$_2$H$_5$)$_2$ | 0.02 / 0.004 / 0.0008 / 0.00016 / 0.000032 | 100 / 100 / 100 / 100 / 100 |
| (6) H$_5$C$_2$S-[aryl]-O-N=C-S-P(OC$_2$H$_5$)$_2$ | 0.02 / 0.004 / 0.0008 / 0.00016 / 0.000032 | 100 / 100 / 100 / 100 / 100 |
| (1) O$_2$N-[aryl]-O-N=C-S-P(OC$_2$H$_5$)$_2$ | 0.02 / 0.004 / 0.0008 / 0.00016 / 0.000032 | 100 / 100 / 100 / 100 / 100 |
| (5) Cl, CH$_3$-[aryl]-O-N=C-S-P(OC$_2$H$_5$)$_2$ | 0.02 / 0.04 / 0.0008 / 0.00016 / 0.000032 | 100 / 100 / 100 / 100 / 100 |

EXAMPLE 6

Test with parasitizing fly larvae

Solvent: 35 parts by weight ethyleneglycolmonomethyl ether.
Emulsifier: 35 parts by weight nonylphenolpolyglycol ether.

To produce a suitable preparation of active compound, 30 parts by weight of the active substance concerned is mixed with the stated amount of solvent which contains the above mentioned proportion of emulsifier, and the concentrate so obtained is diluted with water to the desired concentration.

About 20 fly larvae (*Lucilia cuprina*) are put into a test-tube which contains about 1 cc of horse musculature. 0.5 ml of the preparation of active compound are applied to this horseflesh. After 24 hours, the degree of destruction is determined as a percentage. 100% means that all, 0% that no, larvae have been killed.

The active compound tested, the concentration applied and the test results obtained can be seen from Table 6:

Table 6
(Lucilia cuprina)

| Active compound (constitution) | Concentration of active compound in ppm | Degree of destruction in % |
|---|---|---|
| (9) CH$_3$-[aryl]-O-N=C-S-P(OC$_2$H$_5$)$_2$ | 300 / 100 / 30 / 10 / 3 | 100 / 100 / 100 / >50 / 0 |
| (5) Cl, CH$_3$-[aryl]-O-N=C-S-P(OC$_2$H$_5$)$_2$ | 300 / 100 / 30 / 10 / 3 | 100 / 100 / 100 / 100 / 0 |
| (6) H$_5$C$_2$S-[aryl]-O-N=C-S-P(OC$_2$H$_5$)$_2$ | 300 / 100 / 30 / 10 / 3 / 1 | 100 / 100 / 100 / 100 / <50 / 0 |

Table 6-continued

| Active compound (constitution) | | Concentration of active compound in ppm | Degree of destruction in % (Lucilia cuprina) |
|---|---|---|---|
| (1) | $O_2N$-phenyl-O-N=C(S)-O-P(OC_2H_5)_2 benzisothiazole phosphate | 300 | 100 |
| | | 100 | 100 |
| | | 30 | 100 |
| | | 10 | 100 |
| | | 3 | 0 |
| (8) | $(CH_3)_3C$-phenyl-O-N=C(S)-O-P(OC_2H_5)_2 | 300 | 100 |
| | | 100 | 100 |
| | | 30 | 100 |
| | | 10 | 100 |
| | | 3 | >50 |
| | | 1 | 0 |
| (7) | $O_2N$-phenyl-O-N=C(S)-O-P(OC_2H_5)_2 | 300 | 100 |
| | | 100 | 100 |
| | | 30 | 100 |
| | | 10 | 100 |
| | | 3 | >50 |
| | | 1 | 0 |

EXAMPLE 7

In-vitro test for inhibition of egg deposition by ticks 3 g of active compound are mixed with 7 g of a mixture of equal parts by weight of ethyleneglycolmonomethyl ether and nonylphenolpolyglycol ether. The emulsion concentrate so obtained is diluted with water to the application concentration desired in each case.

Adult, gorged female ticks of the species Boophilus microplus (resistant) are immersed for one minute in this preparation of active compound. After immersion of, in each case, 10 female specimens of the various tick strains, the individual ticks are transferred to plastic dishes, the bottoms of which are covered with filter paper discs.

After 35 days, the effectiveness of the preparation of active compound is determined by ascertaining the inhibition of the deposition of fertile eggs compared with the egg deposition of untreated control ticks. The effect is stated in %, 100% meaning that fertile eggs ceased to be deposited, and 0% meaning that the ticks have deposited eggs in a normal manner like the untreated control ticks.

The results obtained can be seen in the following Table 7:

EXAMPLE 8

Mosquito larvae test

Test insects: Aedes aegypti larvae
Solvent: 99 parts by weight acetone
Emulsifier: 1 part by weight benzylhydroxydiphenyl polyglycol ether To produce a suitable preparation of active compound, 2 parts by weight of the active compound are dissolved in 1000 parts by volume of the solvent containing the amount of emulsifier stated above. The solution thus obtained is diluted with water to the desired lower concentrations.

The aqueous preparations of the active compounds are placed in glass vessels and about 25 mosquito larvae are then placed in each glass vessel.

After 24 hours, the degree of destruction is determined as a percentage. 100% means that all the larvae are killed. 0% means that no larvae at all are killed.

The active compounds, the concentrations of the active compounds, the test insects and the results can be seen from Table 8:

Table 7

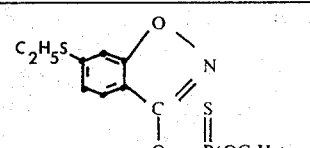

| Active compound (constitution) | Concentration of active compound in ppm | Inhibition of egg deposition in % (Boophilus microplus) | |
|---|---|---|---|
| | | Ridgeland strain | Biarra strain |
| (6) $C_2H_5S$-phenyl-O-N=C(S)-O-P(OC_2H_5)_2 | 10000 | 100 | 100 |
| | 3000 | 100 | 100 |
| | 1000 | 100 | >50 |
| | 300 | >50 | >50 |
| | 100 | <50 | 0 |
| | 30 | 0 | 0 |

Table 8

(Mosquito larvae test)

| Active compound (constitution) | | Concentration of active compound in % | Degree of destruction in % |
|---|---|---|---|
| (B) | [structure: Cl-phenyl with O-N=C(S)-O-P(OC$_2$H$_5$)$_2$ ring] (known) | 0.1<br>0.01 | 100<br>0 |
| (A) | [structure: Cl-phenyl with O-N=C(S)-O-P(OCH$_3$)$_2$ ring] (known) | 1<br>0.1 | 100<br>90 |
| (C) | [structure: Cl-phenyl with O-N=C(O)-O-P(OC$_2$H$_5$)$_2$ ring] (known) | 1<br>0.1 | 100<br>50 |
| (5) | [structure: CH$_3$, Cl-phenyl with O-N=C(S)-O-P(OC$_2$H$_5$)$_2$ ring] | 0.01<br>0.001 | 100<br>30 |
| (1) | [structure: O$_2$N-phenyl with O-N=C(S)-O-P(OC$_2$H$_5$)$_2$ ring] | 0.1<br>0.01 | 100<br>95 |
| (6) | [structure: C$_2$H$_5$S-phenyl with O-N=C(S)-O-P(OC$_2$H$_5$)$_2$ ring] | 0.01<br>0.001 | 100<br>0 |

EXAMPLE 9

LT$_{100}$ test for Diptera

Test insects: *Aedes aegypti*
Solvent: acetone 2 parts by weight of active compound are dissolved in 1000 parts by volume of solvent. The solution so obtained is diluted with further solvent to the desired lower concentrations.

2.5 ml of the solution of active compound are pipetted into a Petri dish. On the bottom of the Petri dish there is filter paper with a diameter of about 9.5 cm. The Petri dish remains uncovered until the solvent has completely evaporated. The amount of active compound per square meter of filter paper varies with the concentration of solution of active compound used. About 25 test insects are then placed in the Petri dish and it is covered with a glass lid.

The condition of the test insects is periodically observed. The time which is necessary for a 100% destruction is determined.

The test insects, the active compounds, the concentrations of the active compounds and the periods of time at which there is a 100% destruction can be seen from the following Table 9:

Table 9

(LT₁₀₀ test for Diptera)

| Active compound (constitution) | Concentration of active compound of the solution in % | LT₁₀₀ |
|---|---|---|
| (7) $O_2N$-[benzisoxazole]-$O$-$P(OC_2H_5)_2$ (with S) | 0.2<br>0.02<br>0.002<br>0.0002 | 60'<br>120'<br>120'<br>180' |
| (B) $Cl$-[benzisoxazole]-$O$-$P(OC_2H_5)_2$ (with S) (known) | 0.2<br>0.02<br>0.002 | 60'<br>120'<br>$3^h = 0\%$ |
| (A) $Cl$-[benzisoxazole]-$O$-$P(OCH_3)_2$ (with S) (known) | 0.2<br>0.02<br>0.002 | 120'<br>180'<br>$3^h = 0\%$ |
| (C) $Cl$-[benzisoxazole]-$O$-$P(OC_2H_5)_2$ (with O) (known) | 0.2<br>0.02<br>0.002 | 60'<br>120'<br>$3^h = 0\%$ |

EXAMPLE 10

LD₁₀₀ test

Test insects: *Sitophilus granarius*
Solvent: acetone 2 parts by weight of the active compound are dissolved in 1000 parts by volume of the solvent. The solution so obtained is diluted with further solvent to the desired concentrations.

2.5 ml of the solution of the active compound are pipetted into a Petri dish. On the bottom of the Petri dish there is a filter paper with a diameter of about 9.5 cm. The Petri dish remains uncovered until the solvent has completely evaporated. The amount of active compound per square meter of filter paper varies with the concentration of the solution of active compound used. 25 test insects are then placed in the Petri dish and it is covered with a glass lid.

The condition of the test insects is observed 3 days after the commencement of the experiments. The destruction is determined as a percentage.

The active compounds, the concentrations of the active compounds, the test insects and the results can be seen from the following Table 10:

Table 10

(LD₁₀₀ test)

| Active compound (constitution) | Concentration of active compound of the solution in % | Degree of destruction in % |
|---|---|---|
| (4) $CH_3$-[benzisoxazole]-$O$-$P(OC_2H_5)_2$ (with S) | 0.002<br>0.0002 | 100<br>0 |
| (7) $O_2N$-[benzisoxazole]-$O$-$P(OC_2H_5)_2$ (with S) | 0.002<br>0.0002 | 100<br>0 |

Table 10-continued

| Active compound (constitution) | (LD$_{100}$ test) Concentration of active compound of the solution in % | Degree of destruction in % |
|---|---|---|
| (1) $O_2N$-[benzisoxazole]-C(O-P(OC$_2$H$_5$)$_2$)=N-S (with C=S) | 0.02<br>0.002 | 100<br>80 |
| (B) Cl-[benzisoxazole]-C(O-P(OCH$_3$)$_2$)=N-S (known) | 0.02<br>0.002 | 100<br>0 |
| (C) Cl-[benzisoxazole]-C(O-P(OC$_2$H$_5$)$_2$)=N (with C=O) (known) | 0.02<br>0.002 | 100<br>0 |

EXAMPLE 11

Critical concentration test/soil insects

Test insect: *Phorbia brassicae* maggots in the soil
Solvent: 3 parts by weight acetone
Emulsifier: 1 part by weight alkylarylpolyglycol ether To produce a suitable preparation of active compound, 1 part by weight of active compound is mixed with the stated amount of solvent, the stated amount of emulsifier is added and the concentrate is diluted with water to the desired concentration. The preparation of active compound is intimately mixed with soil. The concentration of the active compound in the preparatin is of practically no importance; only the amount of active compound per unit volume of soil, which is given in p.p.m. (for example mg/1), is decisive. The soil is filled into pots and the pots are left to stand at room temperature. After 24 hours, the test insects are put into the treated soil and, after a further 48 hours, the degree of effectiveness of the active compound is determined as a percentage by counting the dead and living test insects. The degree of destruction is 100% when all the test insects have been killed; it is 0% when exactly as many test insects are still alive as in the case of the control.

The active compounds, the amounts applied and the results can be seen from the following Table 11:

Table 11

Soil insecticides
(*Phorbia brassicae* maggots in the soil)

| Active compound (constitution) | Degree of destruction in % with a concentration of active compound in ppm of | | | | |
|---|---|---|---|---|---|
| | 20 | 10 | 5 | 2.5 | 1.25 |
| (5) CH$_3$, Cl-[benzisoxazole]-C(O-P(OC$_2$H$_5$)$_2$)=N, C=S | 100 | 98 | 80 | 50 | 0 |
| (12) C$_2$H$_5$S, Cl-[benzisoxazole]-C(O-P(OC$_2$H$_5$)$_2$)=N, C=S | 100 | 90 | 50 | 0 | |
| (B) Cl-[benzisoxazole]-C(O-P(OC$_2$H$_5$)$_2$)=N, C=S (known) | 0 | | | | |

The process of the present invention is illustrated in and by the following preparative example.

EXAMPLE 12

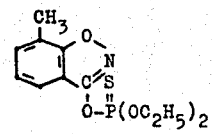
(4)

77 g (0.55 mole) of 3-hydroxy-7-methyl-benzisoxazole dissolved in 950 cc of acetonitrile and 88 g (0.63 mole) of potassium carbonate are stirred for 30 minutes at 40° to 50°C, and 94.5 g (0.5 mole) of 0,0-diethyl-thionophosphoric acid ester chloride are then added to the mixture. The reaction mixture is afterwards stirred for 3 hours at 60° to 70°C, cooled and poured into water; the oil layer which separates is taken up in ether; the ether is washed with a 2 N solution of sodium hydroxide and then with water. After drying, the solvent is evaporated and the residue is "slightly distilled". 134 g (94% of theory) of 0,0-diethyl-0-[7-methylbenzisoxazol(3)yl]-thionophosphoric acid ester are obtained in the form of a yellow oil with refractive index $n_D^{21} = 1.5291$.

| For $C_{12}H_{16}NO_4PS$ (molecular weight 301.2): | | | |
|---|---|---|---|
| | N | P | S |
| Calculated: | 4.65%; | 10.31%; | 10.65%; |
| Found: | 4.61%; | 10.07%; | 10.48%. |

In an analogous manner, the following compounds are prepared:

| | Constitution | Refractive index | Yield in % of theory |
|---|---|---|---|
| (2) | [structure with CH₃, O-P(OCH₃)₂, S] | $n_D^{21}$ : 1.5450 (yellow oil) | 65 |
| (9) | [structure with H₃C, O-P(OC₂H₅)₂, S] | $n_D^{21}$ : 1.5294 (orange-colored oil) | 90.4 |
| (3) | [structure with H₃C, O-P(OCH₃)₂, S] | $n_D^{21}$ : 1.5439 (yellow oil) | 65.3 |
| (5) | [structure with CH₃, Cl, O-P(OC₂H₅)₂, S] | $n_D^{21}$ : 1.5373 (orange-colored oil) | 86.8 |
| (7) | [structure with O₂N, O-P(OC₂H₅)₂, S] | $n_D^{21}$ : 1.5445 (orange-colored oil) | 78.3 |
| (8) | [structure with (CH₃)₃C, O-P(OC₂H₅)₂, S] | $n_D^{21}$ : 1.5230 (yellow oil) | 84.8 |
| (10) | [structure with CH₃, O-P(C₂H₅)(OC₂H₅), S] | $n_D^{21}$ : 1.5410 (yellow oil) | 86.5 |

| Constitution | Refractive index | -continued Yield in % of theory |
|---|---|---|
| (11) [3-methylbenzisoxazol-O-P(=S)(OC₂H₅)(C₂H₅)] | $n_D^{21}$: 1.5413 (orange-colored oil) | 88 |
| (13) [5-nitrobenzisoxazol-O-P(=S)(OC₂H₅)(C₂H₅)] | $n_D^{21}$: 1.5232 (orange-colored oil) | 71 |
| (1) [5-nitrobenzisoxazol-O-P(=S)(OC₂H₅)₂] | $n_D^{21}$: 1.5492 (orange-colored oil) | 71.2 |
| (6) [5-ethylthiobenzisoxazol-O-P(=S)(OC₂H₅)₂] | $n_D^{21}$: 1.5675 (red oil) | 75.3 |
| (14) [5-methylthiobenzisoxazol-O-P(=S)(OC₂H₅)₂] | (yellowish oil) | 75.2 |

EXAMPLE 13

The 3-hydroxybenzisoxazoles required are prepared according to Chem. Ber., Vol. 100, pages 954 to 960 (1967), as follows:

1.00 mole of the appropriate salicylhydroxamic acid is suspended in 400 cc of absolute tetrahydrofurane, and to this suspension there are slowly added dropwise 262 g (2.20 moles) of thionyl chloride with vigorous stirring to maintain the temperature between 25° and 35°C. The mixture is thereafter stirred at 35°C until all solid components are dissolved in about 15 to 30 minutes, then largely concentrated in a vacuum rotary evaporator at a bath temperature of 35°C; the syrup obtained is taken up in 400 cc of absolute dioxane and 303 g (3.00 moles) of triethylamine are added dropwise with vigorous stirring and external cooling. After about one-third of the triethylamine has been added dropwise, the reaction solution thickens to pulp-like consistency and the internal temperature suddenly rises rapidly. Care is to be taken that it does not exceed 30°C. On further dropwise addition, the mixture again liquefies. Finally, the reaction mixture is introduced into 3 liters of water, adding a little triethylamine, if necessary, to ensure that the mixture is alkaline; small amounts of an oily impurity are separated and the clear solution is acidified with concentrated hydrochloric acid. The precipitated reaction product is washed, dried and recrystallized. The yields are 70 to 90% of theory.

In this way, the following starting materials are obtained:

| Constitution | Sublimation point [°C] |
|---|---|
| (15) [5-nitro-3-hydroxybenzisoxazole] | 207 |
| (16) [nitro-3-hydroxybenzisoxazole isomer] | 266 |
| (17) [methylthio-3-hydroxybenzisoxazole] | 147 |
| (18) [methyl-3-hydroxybenzisoxazole] | 163 |
| (19) [tert-butyl-3-hydroxybenzisoxazole] | 168 |

It will be appreciated that the instant specification and examples are set forth by way of illustration and not limitation, and that various modifications and changes may be made without departing from the spirit and scope of the present invention.

What is claimed is:

1. A benzisoxazolo(thiono)phosphoric acid ester selected from the group consisting of:

O,O-diethyl-O-[5-chloro-7-methylbenzisoxazol(3)yl]-thionophosphoric acid ester,

O-ethyl-O-[7-methylbenzisoxazol(3)yl]-thiono-ethane phosphonic acid ester,

O,O-diethyl-O-[7-methylbenzisoxazol(3)yl]-thionophosphoric acid ester, and

O-ethyl-O-[5-methylbenzisoxazol(3)yl]-thiono-ethane phosphonic acid ester.

2. The compound according to claim 1 wherein such compound is O,O-diethyl-O-[5-chloro-7-methylbenzisoxazol(3)yl]-thionophosphoric acid ester of the formula:

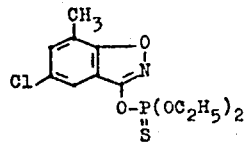 (5)

3. The compound according to claim 1 wherein such compound is O-ethyl-O-[7-methylbenzisoxazol(3)yl]-thiono-ethane phosphonic acid ester of the formula:

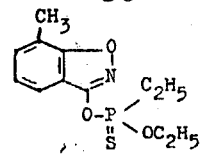 (10)

4. The compound according to claim 1 wherein such compound is O,O-diethyl-O-[7-methylbenzisoxazol(3)yl]-thionophosphoric acid ester of the formula:

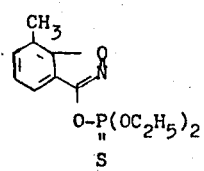 (4)

5. The compound according to claim 1 wherein such compound is O-ethyl-O-[5-methylbenzisoxazol(3)yl]-thiono-ethane phosphonic acid ester of the formula

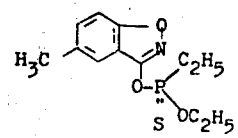

* * * * *